United States Patent
Platt et al.

(10) Patent No.: US 6,485,416 B1
(45) Date of Patent: Nov. 26, 2002

(54) REMOTE MONITORING APPARATUS FOR MEDICAL CONDITIONS

(75) Inventors: Harry Louis Platt, 12 Flower Street, Maroubra, NSW, 2035 (AU); Vladimir Jankov, Randwick (AU)

(73) Assignee: Harry Louis Platt, Maroubra (AU)

( * ) Notice: Subject to any disclaimer, the term of this patent is extended or adjusted under 35 U.S.C. 154(b) by 0 days.

(21) Appl. No.: 09/463,465

(22) PCT Filed: Jul. 24, 1998

(86) PCT No.: PCT/AU98/00591

§ 371 (c)(1),
(2), (4) Date: Mar. 21, 2000

(87) PCT Pub. No.: WO99/04687

PCT Pub. Date: Feb. 4, 1999

(30) Foreign Application Priority Data

Jul. 25, 1997 (AU) .............................................. PO 8265

(51) Int. Cl.⁷ ............................................. A61B 5/0404
(52) U.S. Cl. ........................ 600/300; 128/904; 607/27; 607/32; 600/301
(58) Field of Search ................................ 600/300, 301; 128/904; 607/27, 60, 32, 36, 62

(56) References Cited

U.S. PATENT DOCUMENTS

| | | | |
|---|---|---|---|
| 4,337,377 A | 6/1982 | Van Riper et al. | 179/2 R |
| 4,535,783 A * | 8/1985 | Marangoni | 128/711 |
| 5,172,698 A * | 12/1992 | Stanko | 128/697 |
| 5,317,269 A * | 5/1994 | Mills et al. | 324/427 |
| 5,462,051 A | 10/1995 | Oka et al. | 128/630 |
| 5,544,661 A | 8/1996 | Davis et al. | 128/700 |
| 6,219,408 B1 * | 4/2001 | Kurth | 379/106.02 |

FOREIGN PATENT DOCUMENTS

| WO | 9728736 | 8/1997 |
|---|---|---|
| WO | 9838611 | 9/1998 |

* cited by examiner

Primary Examiner—Kennedy Schaetzle
(74) Attorney, Agent, or Firm—Edwin D. Schindler

(57) ABSTRACT

A physiological monitoring apparatus comprising a cellular phone handset connected to a cellular phone network is disclosed. The handset includes a removable battery container (12) having a physiological monitoring device (14) contained therein as well as a battery power source (13). The battery power source (13) provides power for the operation of the handset (11) as well as providing power for the physiological monitoring device (14). The battery container (12) has detectors (15) located on its outer surface, communicating with the physiological monitoring device (14) through apertres in the battery container (12). Acoustic coupling means (18) are adapted to couple tones produced by the physiological monitoring device (14) with a sound microphone of the cellular phone handset. The physiological monitoring device (14) is activated by placing it against the chest of a patient and the cellular phone handset is used to connect to a remote monitoring station via the cellular phone network. The cellular phone handset sends an electromagnetic signal corresponding to the acoustically coupled tonal signal produced by the physiological monitoring device (14).

12 Claims, 2 Drawing Sheets

REMOTE MONITORING APPARATUS FOR MEDICAL CONDITIONS

The present invention relates to the field of monitoring physiological parameters and, in particular, a cardiac patient's electrical cardiac activity at a central location by means of an apparatus associated with a cellular mobile phone handset and transmitting the information over the cellular phone/ telephone network. The present invention can also be used to measure and control other physiological parameters such as in blood pressure monitoring, asthma control, pregnancy monitoring, oxygen saturation monitoring, diabetes measurement, heart sound monitoring and other like measurements.

BACKGROUND TO THE INVENTION

Although the following description refers generally to remote cardiac monitoring equipment, the equipment can also find utility in any situation in monitoring of other physiological parameters or any other possible use. Therefore, reference to cardiac monitoring is also meant to encompass any monitoring of other physiological parameters where, by suitable modification if necessary, the invention can also be utilised.

Throughout the world, cardiac disease, including heart attack and angina, is the leading. cause of death, It is responsible for more deaths than any other diseases.

It is estimated that 2–4% of the general population suffer from heart disease and 10–12% of the general population are considered to have two or more heart disease risk factors which would ideally require periodic diagnostics or preventive medical treatments.

The activity of the heart is regulated by electrical impulses which can be measured and presented for diagnostic or preventive purposes, in the form of an electrocardiogram (ECG).

To acquire an ECG, electrodes are physically attached to a designated position on the patient's chest to pick up electrical impulses. Traditionally ECG diagnostic tests were carried out in hospitals or clinics where the patient would be attached to an ECG recorder.

Most people experience some form of arrhythmia (abnormal rythym disturbance of the heart). Rarer forms of arrhythmia, such as ventricular fibrillation, often result in the heart stopping and death. According to cardiologists, just under 20% of all people who experience some form of heart attack will die in the first hour due to the severity of the attack.

The most striking fact about survival after heart attacks is the predominance of deaths within the first 24 hours after the attack begins and the significant proportion of these deaths which are within the first few hours. In fact, 60% or more of heart attack deaths occur before the victims reach a hospital. Once victims arrive at hospitals and survive the first day, overall chances of survival are much improved.

Denial time is the time interval between symptom onset and a request for medical care. This so-called denial time contributes greatly to the 3 hour average time lapse between symptom onset and medical intervention. This 3 hour interval is of major significance. It is estimated that each year about 25% of all myocardial infarct patients die before reaching a hospital and that 66% of all sudden deaths occur outside the hospital in the first 2–3 hours after onset of symptoms.

Early therapy, ie within 3 hours of the onset of symptoms, for heart attack victims using anti-clotting agents has shown to significantly increase patient survival rates.

With the development of advanced microprocessors computing and data transmission technologies, the remote transmission and acquisition of ECG is possible presenting new possibilities in home care, preventive diagnosis and emergency systems.

Existing systems for the remote monitoring of a patient's electrical cardiac activity use known ECG equipment which generate tone signals or the like to be sent via a telephone network to a central location which is used to record and monitor the tone signals. The tone signals ire generally acoustically coupled to the telephone handset which transduces the tone signals into electrical signals to be sent over the telephone network.

Existing ECG equipment uses electrodes and wires to provide the electrical signals produced when detected from the patient's cardiac activity. These electrical signals travel over the wires to a transducer device which produces tone signals which are then acoustically coupled to the telephone network, The use of these existing systems is awkward and relatively user unfriendly as the patient is not always in a position or situation where its use is satisfactory or convenient such as when the patient is in public places. The use of the existing ECG equipment including the electrodes and wires also introduces the possibility of errors in the readings due to noise pickup from the wires and electrodes.

It would be advantageous to provide a monitoring apparatus which includes the ECG equipment and telephone handset in the one device so that the apparatus is simple and convenient to use by the cardiac patient in all circumstances as well as dispensing with the need to have the electrodes connected to the equipment by leads or wires which can introduce errors in the readings. It would also be advantageous to have the mobile telephone handset device connected to a cellular mobile telephone network so that the apparatus can be used at public locations which are not accessible by the normal telephone network It would also be advantageous for the mobile cellular phone handset to be used in its normal way as a means for verbal or other communication over the cellular phone network when it is not being used for the remote monitoring of the cardiac activity of the patient.

It would also be advantageous for a monitoring apparatus which includes the other forms of physiological measurement and telephone handset in the one device so that the apparatus is simple and convenient to use by the patient in all circumstances as well as dispensing with the need to have the electrodes or other such detectors connected to the equipment by leads or wires which can introduce errors in the readings.

OBJECT OF THE INVENTION

It is an object of the present invention to provide a physiological monitoring apparatus which substantially overcomes or ameliorates the above mentioned disadvantages. At the very least, the object of the invention is to provide an alternative to known physiological monitoring apparatus.

DISCLOSURE OF THE INVENTION

According to one aspect of the present invention there i s disclose d a physiological monitoring apparatus comprising a cellular phone handset connected to a cellular phone network, said handset including a removable modified battery power source pack container having a physiological monitoring means contained therein as well as a battery power source means, said battery power source means providing power for the operation of the Handset as well as providing power for the physiological monitoring means, said modified battery power source pack container having located on its outer surface detector means are in communication with the physiological monitoring means through apertures in the modified battery power source pack container whereby the detector means are attached to the modified battery power source pack container, acoustic coupling means adapted to couple tones produced by said physiological monitoring means with a sound microphone of the cellular phone handset wherein said physiological monitoring means is activated by placing it against the chest of a patient and said cellular phone handset is used to connect to a remote monitoring station via the cellular phone network, said cellular phone handset sending an electromagnetic signal corresponding to the acoustically coupled tonal signal produced by the physiological monitoring means, Preferably, the physiological monitoring means monitors cardiac activity by means of an electrocardiogram ECG apparatus. The present invention can also be used to measure and control other physiological parameters such as in blood pressure monitoring, asthma and respiratory function control, pregnancy and foetal condition monitoring, oxygen saturation monitoring, diabetes and blood chemistry measurement, heart sound monitoring and other like measurements.

In one preferred form of the invention, the cellular phone connection between the handset and the network is activated by the production of the tonal signal by the ECG monitoring means.

In a preferred form of the invention, the physiological monitoring means monitors signals received from a device implanted in the patient, such as a pacemaker or the like, such that the signals indicate correct functioning thereof.

BRIEF DESCRIPTION OF THE DRAWINGS

The present invention will be now be described with reference to the accompanying drawing in which.

BEST MODE OF CARRYING OUT THE INVENTION

Figure 1:
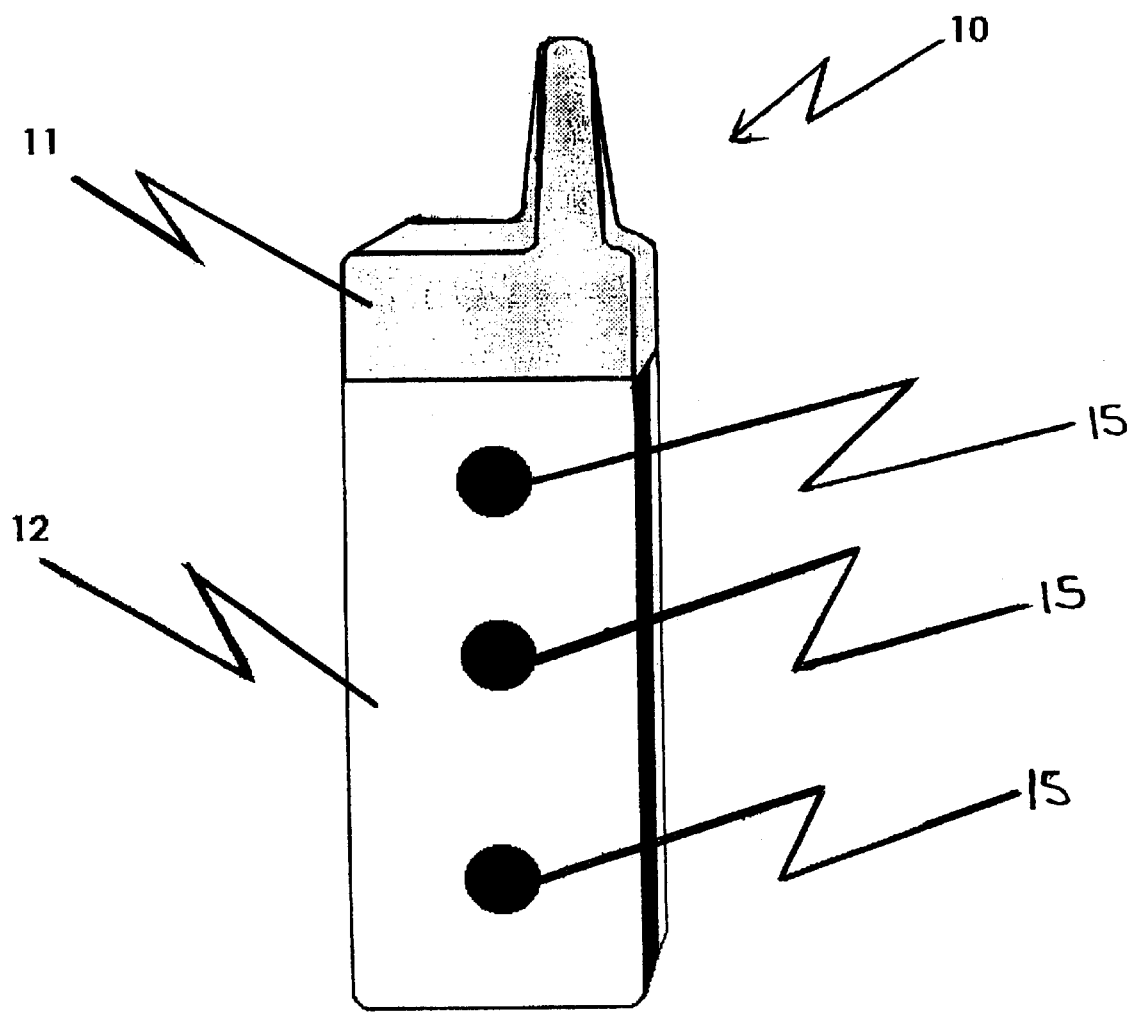
FIG. 1 is a rear perspective view of a cellular phone handset incorporating the apparatus according to the preferred embodiment of the present invention.
Figure 2:
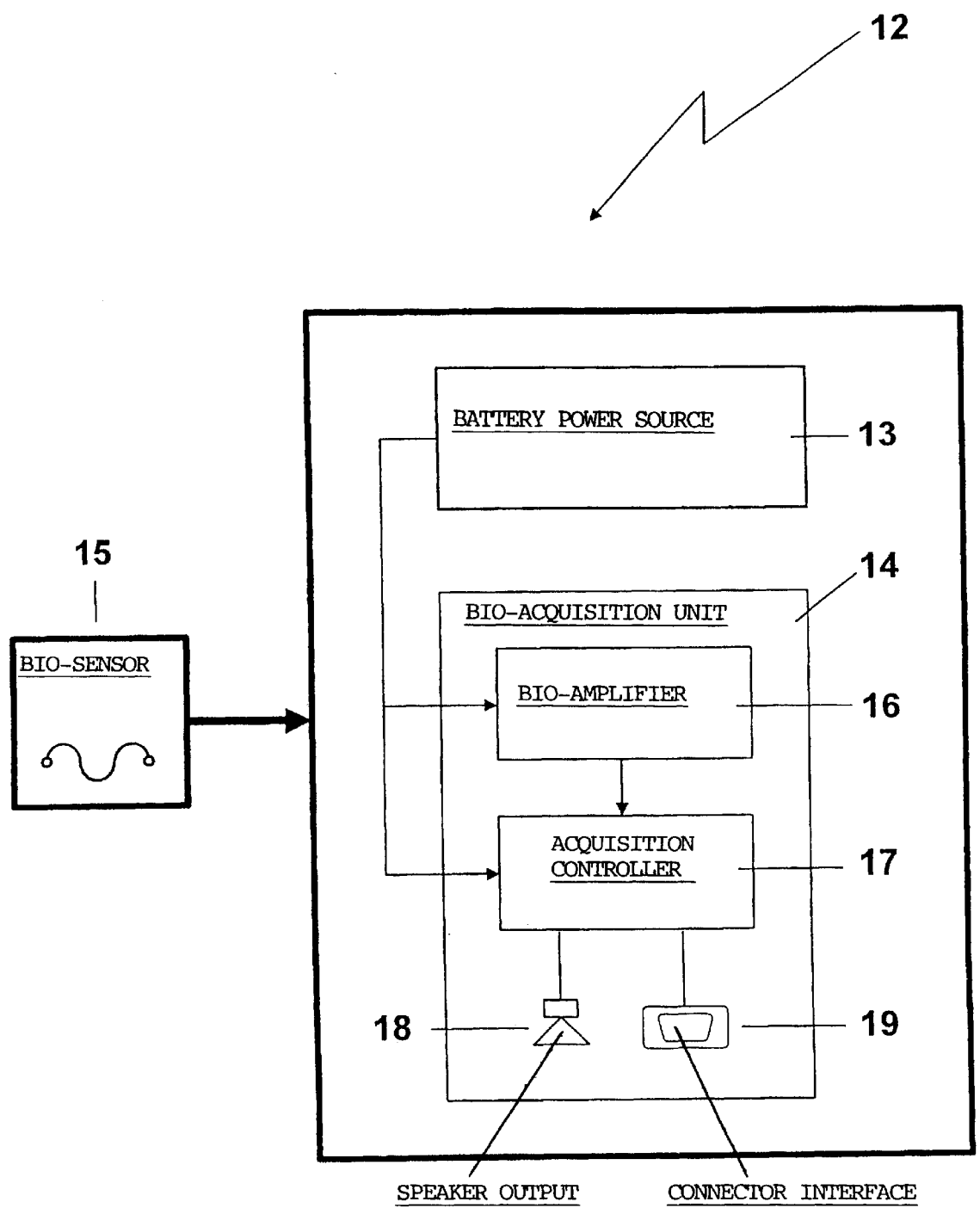
FIG. 2 is a block diagram of the apparatus according to the preferred embodiment of the present invention.

A cellular phone handset 10 incorporating the apparatus of the preferred embodiment is illustrated in the drawings and as Seen from the rear has a casing 11 including a removable modified battery power pack container 12 removably attached thereto.

The battery pack container 12 has contained therein a battery power source 13 together with a bio-aquisition unit 14 which is preferably an ECG monitoring device which formulates the results of electrical cardiac activity detected by a bio sensor 15 which are preferably electrodes which are fixedly attached to the container 12. The bio-aquisition unit 14 includes a bio-amplifier 16 connected to a acquisition controller 17 having a speaker output 18 and a connector interface 19 which is preferably a RS 232 connector. The electrodes 15 connect to the ECG monitoring device 14 via apertures in the container 12. In this embodiment three electrodes 15 are shown, however any number of electrodes can be used according to the specific requirements of the testing of the patient eg cardiac activity etc.

The battery power source 13 is used to power the operation of the ECG monitoring device 14 as well as the operation of the cellular phone handset 10 for its regular use and is able to be charged in the normal way.

The ECG monitoring device 14 produces tone signals corresponding to the signals detected by the electrodes 15 and is acoustically coupled via the speaker output 18 to the microphone of the cellular phone handset 10 which is able to transmit these tone signals over a cellular phone network to a central location which collects and collates these signals as data which is then interpreted by medical practicioners In one preferred form, the ECG monitoring device 14 and cellular phone handset 10 are activated by the receipt of electrical cardiac signals received from the electrodes 15 when the patient places the electrodes against his or her chest in the appropriate manner. The ECG is recorded and simultaneously transmitted to a service centre for diagnostic evaluation after it is received down the "phone line".

The advantages of the apparatus of the preferred embodiment is that the handset 10 with electrodes 15 "built in" provides a simple and convenient method of detecting and transmitting data corresponding to electrical cardiac activity without the possibility of noise and errors being present as is the case with present methods of existing devices. The patient is able to carry a single device in the form of a cellular phone handset and be able to be connected at any time to the central location for analysis of the data.

Naturally the device of the present invention is suitable for the detection of other physiological parameters and use the appropriate detection as required.

In a preferred form of the invention, the physiological monitoring means monitors signals received from a device implanted in the patient, such as a pacemaker or the like, such that the signals indicate correct functioning thereof.

the foregoing describes only one embodiment of the present invention, and modifications obvious to those skilled in the art can be made thereto without departing from the scope of the present invention.

What is claimed is:

1. A physiological monitoring apparatus, comprising:
a cellular telephone handset connected to a cellular telephone network, said cellular telephone handset including a removable modified battery power source pack container having physiological monitoring means contained therein and a battery power source, said battery power source providing power for operating said cellular telephone handset and for providing power for said physiological monitoring means, said modified battery source pack container having an outer surface with detector means located on said outer surface, said detector means being in communication with said physiological monitoring means through apertures in said modified battery power source pack container, so that said detector means is attached to said modified battery power source, said cellular telephone handset further including a sound microphone; and,
acoustic coupling means for coupling tones produced by said physiological monitoring means via said sound microphone of said cellular telephone handset, thereby activating said physiological monitoring means by placing said physiological monitoring means against a patient's chest, said cellular telephone handset being used for connecting to a remote monitoring station via the cellular telephone network, said cellular telephone handset sending an electromagnetic signal corresponding to an acoustically coupled tonal signal produced by said physiological monitoring means, with means for connecting said telephone handset with the cellular telephone network being activated by producing said acoustically coupled tonal signal.

2. The physiological monitoring apparatus according to claim 1, wherein said physiological monitoring means monitoring cardiac activity via an electrocardiogram ECG apparatus.

3. The physiological monitoring apparatus according to claim 1, wherein said physiological monitoring means monitors blood pressure.

4. The physiological monitoring apparatus according to claim 1, wherein said physiological monitoring means monitors respiratory function.

5. The physiological monitoring apparatus according to claim 1, wherein said physiological monitoring means monitors pregnancy and fetal condition.

6. The physiological monitoring apparatus according to claim 1, wherein said physiological monitoring means monitors oxygen saturation.

7. The physiological monitoring apparatus according to claim 1, wherein said physiological monitoring means monitors blood chemistry.

8. The physiological monitoring apparatus according to claim 1, wherein said physiological monitoring means monitors heart sounds.

9. The physiological monitoring apparatus according to claim 1, wherein said physiological monitoring means monitors electrical impulses emanating from a patient's body.

10. The physiological monitoring apparatus according to claim 1, wherein said detector means includes at least one fixedly attached electrode.

11. The physiological monitoring apparatus according to claim 1, wherein said physiological monitoring means monitors signals received from a medical device implanted in a patient with said signals indicating a proper functioning of said medical device.

12. The physiological monitoring apparatus according to claim 11, wherein said medical device is a pacemaker.

\* \* \* \* \*